United States Patent [19]

Kosa et al.

[11] Patent Number: 4,994,059
[45] Date of Patent: Feb. 19, 1991

[54] LASER CATHETER FEEDBACK SYSTEM

[75] Inventors: Nadhir B. Kosa; James J. Burke; Gary L. Moore, all of Minneapolis, Minn.

[73] Assignee: GV Medical, Inc., Minneapolis, Minn.

[21] Appl. No.: 239,602

[22] Filed: Sep. 1, 1988

Related U.S. Application Data

[63] Continuation of Ser. No. 861,459, May 9, 1986, abandoned, which is a continuation of Ser. No. 679,920, Dec. 10, 1984, abandoned.

[51] Int. Cl.⁵ .............................................. A61N 5/06
[52] U.S. Cl. ......................................... 606/12; 606/7; 606/11; 128/398; 356/73.1
[58] Field of Search ...................... 128/633, 634, 303.1, 128/398-401; 356/73.1; 250/227; 606/7, 10, 17

[56] References Cited

U.S. PATENT DOCUMENTS

| | | | |
|---|---|---|---|
| 3,807,390 | 4/1974 | Ostrowski et al. | 128/634 |
| 4,050,450 | 9/1977 | Polyani et al. | 128/634 |
| 4,306,877 | 1/1981 | Lübbers | 128/633 |
| 4,311,142 | 1/1982 | Machida | 128/303.1 |
| 4,320,939 | 3/1982 | Mueller | 350/312 |
| 4,385,832 | 5/1983 | Doi et al. | 356/73.1 |
| 4,403,143 | 9/1983 | Walker et al. | 250/227 |
| 4,409,476 | 10/1983 | Löfgren | 250/227 |
| 4,423,726 | 1/1984 | Imagawa et al. | 128/303.1 |
| 4,476,512 | 10/1984 | Sunago et al. | 128/303.1 |
| 4,492,121 | 1/1985 | Lehto | 250/227 |
| 4,543,477 | 9/1985 | Doi et al. | 356/73.1 |
| 4,582,809 | 4/1986 | Block et al. | 356/73.1 |
| 4,695,697 | 9/1987 | Kosa | 219/121 LZ |
| 4,716,288 | 12/1987 | Doi | 128/303.1 |
| 4,716,501 | 12/1987 | McKee et al. | 362/326 |

FOREIGN PATENT DOCUMENTS

| | | | |
|---|---|---|---|
| 28669 | 5/1981 | European Pat. Off. | 356/73.1 |
| 3411229 | 10/1985 | Fed. Rep. of Germany | 356/73.1 |
| 2453403 | 12/1980 | France | 356/73.1 |
| 2493533 | 5/1982 | France | 128/303.1 |
| 2493559 | 5/1982 | France | 128/303.1 |
| 146652 | 12/1978 | Japan | 356/73.1 |
| 57-222 | 4/1982 | Japan | 356/73.1 |
| 77936 | 5/1982 | Japan | 356/73.1 |
| 93228 | 6/1982 | Japan | 356/73.1 |
| 70140 | 4/1983 | Japan | 356/73.1 |
| 58404 | 4/1984 | Japan | 356/73.1 |
| 23934 | 2/1986 | Japan | 356/73.1 |
| 2113837 | 8/1983 | United Kingdom | 374/161 |

OTHER PUBLICATIONS

"Visualization of Optical Fields Propagating in Integrated Optical Waveguides" by D. Ostrowsky et al; Proc. Symp. on Opt. and Acoust., Micro-Electronics, Polytechnic Inst. of New York, Apr. 16-18, 1974, pp. 451-457.

"52 KM-Long Single Mode Optical Fibre Fault Location Using the Stimulated Raman Scattering Effect" by K. Noguchi et al; Electronics Letters; Jan. 7, 1982, vol. 18, No. 1, pp. 41-42.

Primary Examiner—Max Hindenburg
Assistant Examiner—David Shay
Attorney, Agent, or Firm—Orrin M. Haugen; Thomas J. Nikolai; Frederick W. Niebuhr

[57] ABSTRACT

A control system for a laser catheter device wherein the control system is provided with means for determining the intensity of laser beam energy at two points, one of which is at the distal tip end thereof, and with the other being interposed along a transmitting column remote from both the source of laser beam energy and the distal tip. A beam splitter means(dichroic filter) is provided for diverting a first portion of the laser beam energy onto a first detector means. Energy passing through the beam splitter is ultimately directed onto a fluorescent member or device disposed adjacent the distal tip, with the fluorescent member or means being capable of emitting or generating radiant energy at a wavelength significantly different from that of the incident laser beam energy. The radiant energy generated by the fluorescent means is directed onto a second surface of the beam splitter means, and ultimately onto a second detector means. First and second signal processing means responsive to the first and second detector means are utilized to control a shutter, such as a dual shutter, which is arranged to interrupt the passage of laser beam energy through the catheter system upon the occurrence of anomalous levels of laser beam energy at either the first or second detector means.

4 Claims, 2 Drawing Sheets

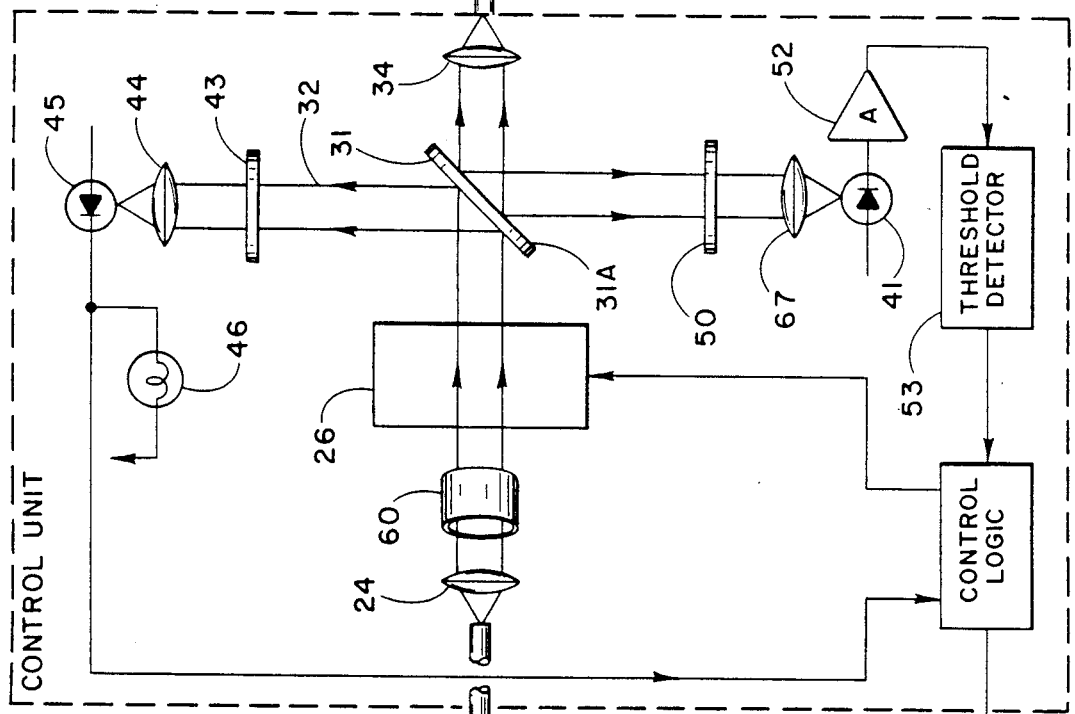
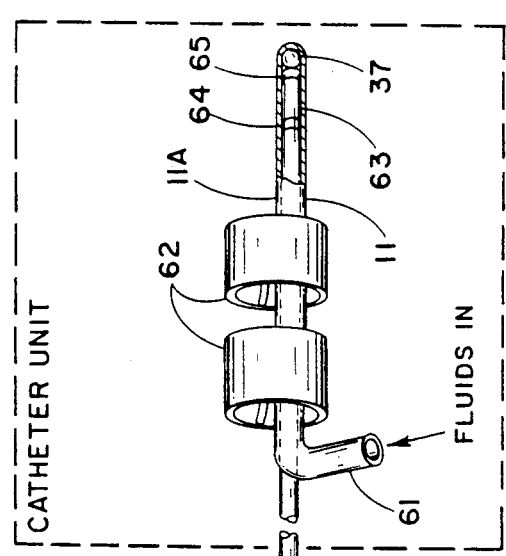
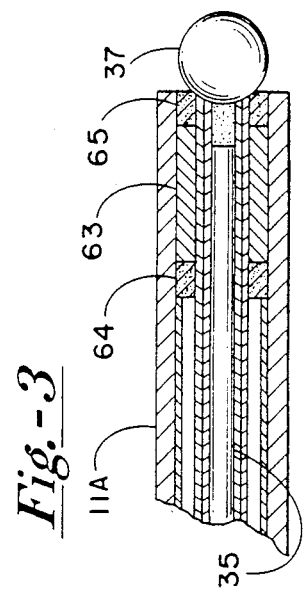

LASER CATHETER FEEDBACK SYSTEM

This is a continuation of application Ser. No. 06/861,459, filed May 9, 1986, abandoned which was continuation application of patent application Ser. No. 06/679,920, filed Dec. 10, 1984, now abandoned.

BACKGROUND OF THE INVENTION

The present invention relates generally to an improved control system for a laser enhanced transluminal catheter device, and more particularly to a such a control system utilizing an optical feedback system capable of monitoring the output intensity or energy of the laser beam at the distal tip of the catheter. The feedback signal is normalized relative to that level detected at a point disposed relatively close to the laser generator component per se.

The control system of the present invention is particularly adapted to a laser enhanced transluminal angioplasty catheter wherein obstructions in blood vessels may be treated with exposure to laser energy to obtain either a partial reduction and/or elimination of the obstruction by means of such exposure. An optical fiber is utilized for transmitting the laser beam energy from the generator onto the obstruction located in the zone to be treated. The optical fiber can also be utilized for the purpose of providing illumination and optical viewing. Laser enhanced transluminal angioplasty catheter devices are considered valuable tools for the treatment of commonly encountered forms of arteriosclerosis and the like.

Atheroclerosis is among the more commonly encountered forms of arteriosclerosis as it relates to the human heart and circulatory system, which typically has been treated by drugs, angioplasty catheterization, and also through open heart bypass surgical procedures. Of these various forms of treatment, angioplasty catheterization has been found to be a treatment of choice in certain situations. Such treatment normally involves initially bringing a balloon-tipped catheter proximate the material forming the obstruction matter in the vessel, with the distal tip catheter normally being forced through the obstruction and the balloon portion is thereafter inflated so as to cause dilation of the obstruction. This procedure is effective in reopening the blood vessel and restoring substantially normal circulation in many cases. This procedure is, however, especially dependent upon the skill of the cardiologist, and particularly as that skill pertains to manipulation and ultimate direction and control of the catheter. Normally, some assistance is provided through fluoroscopy techniques, typically through the incorporation of radiopaque members along the catheter. It is further recognized that angioplasty catheterization is frequently a procedure limited to those patients having obstructions which have not totally occluded the blood vessels to the point where the nominal diameter of the distal tip of the catheter would otherwise prevent passage of the catheter through the obstruction prior to dilation of the vessel.

Because of its application to surgical procedures, laser enhanced transluminal angioplasty catheters have been developed. In such devices, the catheter is provided with a source of laser energy, and this laser energy is directed to the site along optical fibers. One such laser enhanced transluminal angioplasty catheter device is disclosed in copending application, Ser. No. 560,234, filed Dec. 12, 1983 and entitled "LASER TRANSLUMINAL ANGIOPLASTY CATHETER" and assigned to the same assignee as the present invention.

By way of background, dilating catheters are known, having been disclosed in U.S. Pat. Nos. 4,040,413; 4,271,839; and 4,299,226. Catheter devices including optical fibers are disclosed in U.S. Pat. Nos. 3,123,066; 3,136,310; 3,858,577; 4,146,019; and 4,273,019. Also, laser enhanced catheters are disclosed in U.S. Pat. Nos. 3,467,098; 3,538,919; 3,843,865; and 4,266,548.

As set forth in co-pending application Ser. No. 560,234 described above, a laser transmitting transluminal angioplasty catheters is disclosed. An additional example of multi-technology catheters is described in U.S. Pat. No. 4,207,874 and/or the *American Journal of Cardiology*, 50:80, 81 (Dec. 1982). In U.S. Pat. No. 4,207,874, and of which the *American Journal of Cardiology* article is an elaboration, a fiber optic directable catheter is disclosed, with the device including a bundle of laser transmitting fibers and a centrally disposed lumen for permitting the suction removal of vaporized waste material after exposure to laser beam energy. Upon completion of the tunneling procedure, blood samples which are collected in a transparent external collection reservoir visually indicate the extent of completion of the procedure to the operator.

In laser enhanced transluminal angioplasty catheter devices, it is desirable for the operator to determine and to be reasonably confident that the laser energy being directed to the site is within certain predetermined desirable limits, that is, the energy is known to exceed a certain base or minimum threshold level, while not exceeding a certain upper limit. An indication that the laser beam energy is within predetermined limits will enable the procedure to be more reliable, expedient, reproducible, and efficacious. Inasmuch as optical fibers are being employed, along with other electro-mechanical and optical systems, proper evaluation of the operating parameters is desired. For example, the rupture, fracture, or occurrence of damage to the optical fiber may reduce the energy level available at the distal tip of the catheter to such an extent that the procedure would be generally ineffective. On the other hand, excessive quantities of laser beam energy available at the distal tip of the catheter may adversely affect the quality of the procedure.

The present invention utilizes a control system which is interposed along the optical fiber segments which are provided to transmit laser energy from the generator to the distal tip. The control system includes an electromechanical shutter and a beam splitter disposed along the beam path. An attenuator and a focusing lens are located orthogonal to the energy beam, and a predetermined proportion of the energy is reflected and/or sampled by the beam splitter and directed into the attenuator and focusing lens and onto a first detector. The detector is in turn coupled to a power level monitor. On the catheter side of the beam splitter, and also orthogonal to the beam, is an interference filter and a second focusing lens. At the distal tip of the optical fiber there is disposed a fluorescent element. The term "fluorescent" is intended to be used in a comprehensive sense, such as the response generated in such an element when irradiated with electromagnetic radiation of a given wavelength, with the response being the emission of radiation at a second and longer wavelength. One particularly desirable optically reactive device is a sapphire doped to fluoresce when transmitting laser energy. Since the fluorescent energy which is generated by the incident laser energy is at a wavelength significantly different from that of the laser energy, the fluorescent energy is transmitted or reflected back through the optical fiber and onto the catheter facing surface of the beam splitter. The fluorescent energy is then reflected by the catheter facing surface of the beam splitter (dichroic filter) into a focusing lens and thence onto a second detector. The output of the second detector is typically amplified and fed into a threshold detector. The output of the threshold detector is, in turn, coupled to the shutter system as well as to the power supply of the laser generator.

In the event the distal portion and/or distal tip of the optical fiber becomes damaged, the quantity or output of fluorescent energy generated by the optically reactive means will become diminished and the threshold detector will respond to the drop with a reduction in signal amplitude. This change, as detected, will create a signal which may be fed through a feedback loop which will, in turn, either shut off the laser generator and/or close the shutter system. The system of the present invention permits simultaneous monitoring of the output of the laser generator and the output of the optical fiber. In certain applications, an attenuator may be placed in the laser beam path in front of the shutter system. The ratio of the optical fiber output relative to the laser generator output is monitored continuously, and in the event the ratio falls outside of a predetermined range because of a failure of a system component, the entire system may be automatically shut down.

SUMMARY OF THE INVENTION

In accordance with the present invention, a system is provided for feedback of information from the distal tip of the catheter without the need for additional optical fibers or wires to be employed in the catheter. Furthermore, the fiber optic tip at the end of the catheter is properly protected. The system of the present invention further allows simultaneous measuring and/or comparing of the laser generator output and the catheter output, with the response time of the feedback system being extremely fast for proper system monitoring. In the event of a malfunction, or if the output deviates from a pre-established or predetermined range, the system may be immediately shut down.

In addition to the control function, the placement of a fluorescing lens at the distal tip of the optical fiber provides a convenient means for focusing and/or diverging the laser beam energy. This lens also provides protection for the tip of the optical fiber. Such a lens also makes it possible to monitor the temperature level existing at the distal tip of the optical fiber. Temperature monitoring is an available feature which may be accomplished by intermittent pulsing of the laser along with a measurement of the response time of the incident fluorescent energy. The output of the catheter may be monitored relative to the laser output so as to assure operation at the appropriate and desired level.

Therefore, it is a primary object of the present invention to provide an improved feedback control system for laser enhanced transluminal angioplasty catheter devices, wherein the control system provides a means for monitoring the energy level available from the laser generator, as well as that available at the distal tip of the laser enhanced catheter through feedback from the distal tip.

It is a further object of the present invention to provide an improved laser enhanced transluminal angioplasty catheter device which provides a means for monitoring the laser output at the distal tip of the catheter relative to the output of the laser generator, and with the control system employing a feedback arrangement from the distal tip of the catheter without requiring the presence of any additional optical fibers or wires in the catheter to accomplish the monitor function.

It is yet a further object of the present invention to provide a control system for a laser enhanced transluminal angioplasty catheter device which employs a feedback system having a rapid response which is adapted for monitoring the output at the distal tip of the catheter, and which will shut the system down in the event the output deviates from pre-established ranges.

Other and further objects of the present invention will become apparent to those skilled in the art upon a study of the following specification, appended claims, and accompanying drawings.

DESCRIPTION OF THE DRAWINGS

FIG. 2 is a schematic diagram illustrating the details of the optical unit utilized in the laser enhanced transluminal angioplasty catheter feedback system with the energy feedback being available from the distal tip of the catheter; and FIG. 3 is a fragmentary detail schematic diagram of the distal tip portion only of the catheter assembly.

DESCRIPTION OF THE PREFERRED EMBODIMENT

Figure 1:
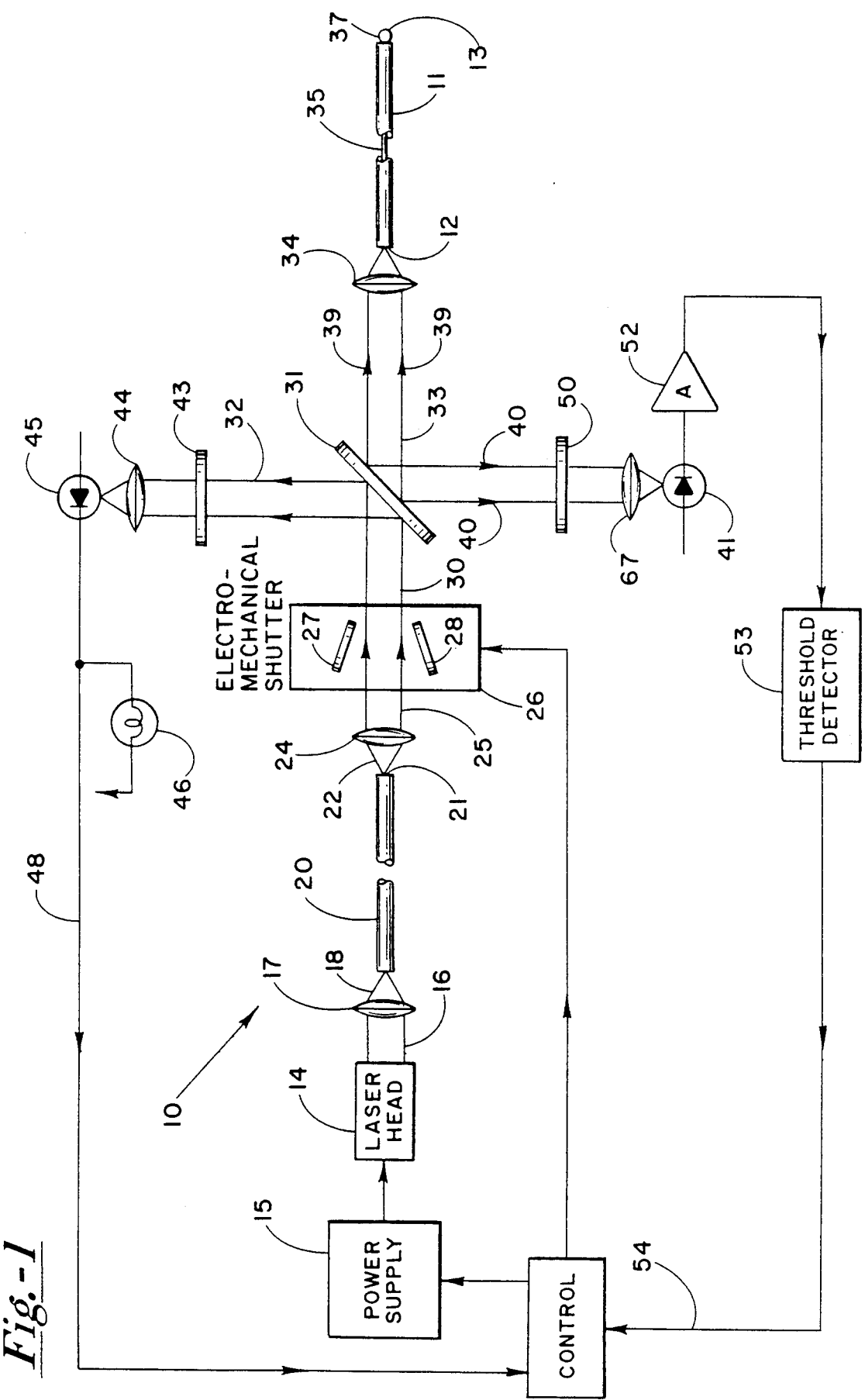
FIG. 1 is a schematic diagram illustrating one embodiment of the present invention, and illustrating the manner in which the control system simultaneously monitors or measures the output energy from the laser generator, as well as the energy received through the transmission system and accordingly available at the distal tip of the catheter.

In accordance with the preferred modification of the present invention, and with particular attention being directed to FIG. 1 of the drawings, the laser enhanced transluminal angioplasty catheter system generally designated 10 includes a transluminal angioplasty catheter member 11 having a proximal end 12 and a distal tip end 13, and with the catheter incorporating optical fibers for transmission of laser beam energy therethrough. Laser energy is provided from laser head 14, driven by power supply and control 15. Laser heads for the generation of laser energy for laser enhanced transluminal angioplasty catheter devices are commercially available, as are power supply and control sytems therefore. The energy generated at the laser head 14 is transmitted through the wall of the head, along column 16, and into focusing lens 17. Focusing lens 17 directs the energy along the column shown as at 18, and into a first optical fiber segment as at 20. Optical fiber 20 is of a convenient length, such as a length of, for example, 10 meters. The terminal end 21 of optical fiber segment 20 is designed to pass laser energy along an energy cone as at 22, and into focusing lens 24. The beam passing through lens 24 is preferably arranged in a collimated form or parallel path as at 25, and passed into electromechanical dual shutter 26. In normal operation, dual shutter 26 permits the beam to pass therethrough, as is indicated in FIG. 1, and in the event of any malfunction as will be described hereinafter, electromechanical dual shutter 26 will close its panel members or vanes 27 and 28 so as to interrupt the passage of laser beam energy therethrough. The laser energy exiting shutter 26 is shown in beam form 30, and passes onto beam splitter 31. Beam splitter 31 may conveniently be and is preferably a dichroic filter arranged for substantial or maximum transmission of incident laser beam energy. The small portion or sample of incident laser energy which is reflected off the surface of beam splitter 31 is indicated as at 32, with the balance of the energy passing through splitter 31 and along beam column shown at 33. Beam column 33 passes through focusing lens 34, and into a second segment of optical fibers 35 contained within a lumen formed in laser enhanced transluminal angioplasty catheter 11. At the distal tip of the catheter 11 is a fluorescent element or means for generating radiant energy at a wavelength significantly different from that of the incident laser beam energy. Typically, the fluorescent means may be a sapphire element containing a dopant which generates fluorescent energy or other radiant energy which is emitted at a wavelength significantly different from that of the incident laser beam energy. The sapphire element, such as optically reactive or doped sapphire element 37 is, of course, commercially available. One such useful dopant is chromium. While a sapphire element containing a dopant has been found to be desirable for use as the material of construction for element 37, it will, of course, be appreciated that other fluorescent substances may be employed as well. It is desirable that the material be highly transmissive to energy within the wavelength of the laser beam, and further that it have the property of generating fluorescent energy or other detectable radiant energy at a wavelength significantly different from that of the incident laser beam energy.

The radiant energy generated by the fluorescent sapphire element 37 is received by and passed along optical fiber 35, in the direction indicated by arrows 39—39, and onto the catheter facing surface of beam splitter 31. The beam splitter (dichroic filter) which in this case, reflects the energy of the wavelength generated by the fluorescent member, passes along the path indicated by arrows 40—40 and ultimately received at the active surface of detector 41. This portion of the apparatus will be described in detail hereinbelow.

Turning now to the means for monitoring incident laser light from the laser generator or head 14, this sample of the overall output energy of the laser passes along beam column 32 through attenuator 43, focusing lens 44, and onto the active surface of radiant energy detector 45. A power level indicator as at 46 is in circuit with detector 45, thus providing an indication of the power level of incident laser energy received at the incoming surface of beam splitter 31. Furthermore, the output of detector 45 is coupled along line 48 to power supply and power control 15 through the control logic. Detectors such as detector 45, power level indicator 46, and the corresponding input to power supply and control 15 are commercially available.

Turning now to the reflected light which is generated by optically reactive member 37, received upon and transmitted from the second surface of beam splitter 31, such as is shown at 40-40, an interference filter is shown in the path as at 50, with this filter being adapted for maximum transmission of incident radiation at about 6940 Angstroms. This filter will typically have its peak transmission at the range of maximum generation of the optically reactive member 37. The signal generated by detector 41 is passed through a typical pre-amplifier as at 52, for transmission to threshold detector 53. The output of threshold detector 53 is normalized with respect to the output laser energy detector and is transmitted to separate logic controls, one being an input to electromechanical dual shutter 26, the other being an input, as at 54, to power supply and control 15. As has been previously indicated, if the normalized output of threshold detector 53 is outside of prescribed and desired limits, the active vanes 27 and 28 of shutter 26 are closed so as to totally interrupt and shut down the transmission of laser beam energy into the catheter 11.

It will be appreciated, therefore, that the laser beam energy passing between focusing lens 24 and focusing lens 34 is, in effect, passing through an evaluation zone for controlling the amount of energy available in the overall system, and also available at the distal tip of the laser enhanced transluminal angioplasty catheter 11.

Attention is now directed to FIG. 2 of the drawings wherein the optical unit for the laser catheter is shown in greater detail. Similar numerals are utilized to identify similar items from that shown in FIG. 1 where practical.

In the system of FIG. 2, and within the laser unit block is laser head 15A driven by power supply 15B so as to generate a column of laser beam energy as at 16. Focusing lens 17 provides a means for focusing and directing the beam into the first optical fiber segment as at 20, with segment 20 being typically 10 meters in length.

The control unit block commences generally at the terminal end of the first optical fiber segment, as also shown in FIG. 1. Lens 18 is employed to collimate the beam and pass the beam through an attenuator 60. Attenuator 60 is utilized to control the amount of the transmitted power through the system. Light passing through attenuator 60, as previously indicated, passes through electromechanical dual shutter 26 and onto the first surface of beam splitter 31. In this embodiment, beam splitter 31 is a dichroic filter, with such dichroic filters being, of course, commercially available. Dichroic filter 31 is selected so as to provide for maximum transmission of laser light, with only a small percentage being reflected along path 32, as previously set forth in the embodiment of FIG. 1. Attenuator 43 is employed to control the amount of energy incident to and received upon detector 45. The output from detector 45, as indicated previously, is conveniently displayed on power level indicator 46, and ultimately received at the first control input 15C to power supply 15B.

The laser enhanced transluminal angioplasty catheter 11 as illustrated in FIG. 2 is provided with one or more additional lumens for the transmission of fluids, with the lead-in to the fluid transmitting lumen being shown at 61. A protective shield or tubing for catheter 11 is illustrated at 62, with the tubing for the laser enhanced transluminal angioplasty catheter device 11 being preferably formed of an FDA approved material or substance such as, for example, polyethylene or equivalent. A metallic or glass sleeve is provided at 63 for receiving optical fibers and the sapphire element. In the application of a glass tube, additional radiopaque bands, such as at 64 and 65, are employed in order to assist in determining and viewing the location of the distal tip portion of laser enhanced transluminal angioplasty catheter 11, and also, in certain instances, may be utilized to locate the position of the distal tip of the optical fiber portions in those systems wherein the optical fibers may extend beyond the distal tip of the catheter sleeve portion, such as beyond polyethylene sleeve portion 11A.

In order to protect the surface of fiber or fibers 35, a buffer sheath may be utilized to encapsulate or coat the outer surface. Typically, this buffer layer may be one or more films or layers of a polyamide material, and may, in certain instances, contain a UV marker additive. Also, in certain applications, it may be desirable to provide an inner buffer film or layer for the polyethylene sleeve portion 11A. Such material may be formed of a compatible polymeric material such as an epoxy material or the like. It may be desirable, in certain instances, to provide this inner film or layer with a UV marker.

With attention being directed to FIG. 3, and because of limitations of draftsmanship, the individual multi-layer arrangements are illustrated in fragmentary cutaway form.

As illustrated in FIG. 1, reflected light from optically reactive and responsive element 37 is reflected from surface 31A of beam splitter (dichroic filter) 31 and through interference filter 50 and through focusing lens 67 and into detector element 41. The output of threshold detector 53, as previously indicated in connection with the embodiment of FIG. 1, provides inputs to electromechanical shutter 26 as well as to power supply 15B, such as at the second control input 15D to power supply 15B.

As an alternate layout for the system, beam energy from the laser unit may be passed directly onto a beam splitter, with first and second detectors being employed to deliver signals to the control monitor, such as an electromechanical shutter system. On the catheter side of the beam splitter, a focusing lens is provided to carry the laser beam energy into the input of a first optical fiber segment, which terminates through connectors into the control monitor. The output from the control monitor is, in turn, delivered into the second optical fiber segment, and thence into the distal tip end of the catheter unit. Such an arrangement provides an advantage of employing one less alignment mechanism, and eliminates certain lenses.

The laser enhanced transluminal angioplasty catheter device with the feedback system as disclosed herein is advantageously utilized in such catheter devices, since it is highly reliable, and is utilized without need for additional fibers or wires in the catheter structure.

We claim:

1. In a laser enhanced transluminal angioplasty catheter system including a catheter having a proximal end and a distal end, a laser beam generator providing a source of laser beam energy, lens means for focusing the laser beam energy from the source onto an optical fiber column for providing a beam transmitting fiber column for transmission of laser beam energy along said catheter from the proximal end of the distal tip end thereof and a control means for controllably interrupting the delivery of laser beam energy to said optical fiber column being interposed along said fiber column at the proximal end of said catheter, said laser enhanced transluminal angioplasty catheter system being characterized in that:

(a) an optical fiber column extends along the length of said catheter system for transmitting said laser beam energy to the distal tip of said catheter for controllably discharging said laser beam energy from said catheter distal tip, said control means including a laser beam energy evaluation zone at the proximal end of said catheter system between said generator means and said distal tip, and means for accessing at least a portion of said laser beam energy within said beam energy evaluation zone during operation of said laser beam generator and said catheter system;

(b) said optical fiber column including means for delivering laser beam energy from said column to said laser beam evaluation zone;

(c) said control means including shutter means within said beam energy evaluation zone and having means for controllably interrupting the passage of laser beam energy through said beam energy evaluation zone and along said beam transmitting fiber column upon detection of an anomalous signal from said control means;

(d) beam splitter means disposed within said beam energy evaluation zone for diverting a portion of said laser beam energy passing through said beam energy evaluation zone for directing said diverted portion onto a first detector means, and means for simultaneously enabling the passage of the non-diverted portion of said laser beam energy through said beam splitter means and along said beam transmitting fiber column to said distal tip;

(e) optically reactive means disposed at the distal tip of said catheter along the path of the non-diverted portion of said laser beam energy and axially distally of said beam transmitting fiber column for normally receiving and normally transmitting substantially all of said non-diverted laser beam energy therethrough, and having optically reactive fluorescent responsive means incorporated therein for fluorescing to generate radiant energy at a wavelength significantly different from that of said laser beam energy while being stimulated with said laser beam energy transmitted along said beam transmitting fiber column and received by said optically reactive means, said optically reactive means being a fluorescent lens element which emits fluorescent energy upon stimulation by laser beam energy;

(f) means for simultaneously transmitting said stimulated radiant energy from said optically reactive means as an energy source through said beam transmitting fiber column and thence onto said beam splitter means for diversion of said stimulated radiant energy onto a second detector means during the operation of said laser beam generator and with said beam transmitting fiber column simultaneously transmitting laser beam energy created by said laser beam generator to said optically reactive means;

(g) first and second signal processing means responsive to said first and second detector means respectively; and (h) said control means further including shutter control means responsive to the output of said first and second signal processing means for closing said shutter means and interrupting the passage of laser beam energy from said laser beam generator through said beam energy evaluation zone upon detection of an anomalous signal form one of said first and second detector means.

2. The laser enhanced transluminal angioplasty catheter system as defined in claim 1 being particularly characterized in that said beam splitter means is a dichroic filter arranged for maximum transmission of incident laser beam energy.

3. The laser enhanced transluminal angioplasty catheter system as defined in claim 1 being particularly characterized in that said fluorescent lens element contains a dopant and is arranged to fluoresce and emit fluorescent energy at a wavelength greater than that of the incident laser beam energy.

4. The laser enhanced transluminal angioplasty catheter system as defined in claim 1 being particularly characterized in that said optical fiber column is arranged in first and second spaced apart fiber optical segments, and wherein said beam energy evaluation zone is interposed between said first and second spaced apart fiber optical segments.

* * * * *

UNITED STATES PATENT AND TRADEMARK OFFICE
CERTIFICATE OF CORRECTION

PATENT NO. : 4,994,059

DATED : February 19, 1991

INVENTOR(S) : Nadhir B. Kosa et al

It is certified that error appears in the above-identified patent and that said Letters Patent is hereby corrected as shown below:

Column 8, line 59, "form" should read -- from --.

Signed and Sealed this

Thirtieth Day of June, 1992

Attest:

DOUGLAS B. COMER

*Attesting Officer*  *Acting Commissioner of Patents and Trademarks*